(12) United States Patent
Girardot et al.

(10) Patent No.: US 6,315,482 B1
(45) Date of Patent: *Nov. 13, 2001

(54) APPLICATOR FOR APPLYING AND DISTRIBUTING SUBSTANCES TO TARGET SURFACES

(75) Inventors: Richard Michael Girardot; Gene Michael Altonen, both of West Chester; Lyle Brown Tuthill, Indian Hill; Curtis Bobby Motley, West Chester, all of OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/185,785

(22) Filed: Nov. 4, 1998

(51) Int. Cl.$^7$ ................................... B05C 11/00

(52) U.S. Cl. .................. 401/266; 401/261; 15/104.93

(58) Field of Search ................................ 401/88, 49, 6, 401/261, 139, 196, 200, 201, 266, 264, 265; 32/35; 15/104.93, 104.24, 244.4

(56) References Cited

U.S. PATENT DOCUMENTS

| | | |
|---|---|---|
| 926,462 | 6/1909 | Blowers . |
| 1,431,210 | 10/1922 | Blanchard . |
| 1,511,969 | * 10/1924 | Hoy ........................................ 401/196 |
| 1,690,960 | 11/1928 | Yamanaka . |
| 1,705,249 | 3/1929 | Henry . |
| 1,836,833 | 12/1931 | Ames . |

(List continued on next page.)

FOREIGN PATENT DOCUMENTS

| | | |
|---|---|---|
| 196 33 687A1 | 2/1998 | (DE) . |
| 0 028 853 | 5/1981 | (EP) . |
| 0 600 508A1 | 6/1994 | (EP) . |
| 0 732 273B1 | 9/1996 | (EP) . |
| 0 803 210A1 | 10/1997 | (EP) . |
| 797369 | 4/1936 | (FR) . |
| 2 601 865 | 1/1988 | (FR) . |
| 1477781 | * 3/1966 | (FR) ............................. 401/196 |
| 1454403 | 11/1976 | (GB) . |
| WO 96/04884 | 2/1996 | (WO) . |
| WO 97/28718 | 8/1997 | (WO) . |

*Primary Examiner*—David J. Walczak
(74) *Attorney, Agent, or Firm*—Jack L. Oney, Jr.

(57) ABSTRACT

Applicator for applying and distributing a substance onto a target surface. The applicator comprises a substantially planar sheet of compressible, conformable material having opposed first and second surfaces and an interior region between said first and second surfaces. The sheet of material has a thickness between the first and second surfaces which decreases when the sheet of material is subjected to an externally-applied force in a direction substantially normal to the first surface. The applicator further includes at least one discrete reservoir extending inwardly of the first surface into the interior of the sheet of material which is at least partially filled with a substance and at least one discrete aperture formed in the first surface which is in fluid communication with the reservoir. Compression of the sheet of material via an externally-applied force substantially normal to said first surface expresses product from the aperture and translational motion of the first surface relative to a target surface applies and distributes said product onto the target surface. In a preferred embodiment, a plurality of apertures are associated with corresponding reservoirs forming a delivery zone near one end of a hand-held applicator, and the sheet material is preferably resilient both in compression and in bending to conform to irregular target surfaces. A wide variety of substances are contemplated, including particularly antiperspirant/deodorant products. Other embodiments include a single reservoir feeding a plurality of apertures.

24 Claims, 2 Drawing Sheets

U.S. PATENT DOCUMENTS

| | | | |
|---|---|---|---|
| 1,925,019 | 8/1933 | Wilson | 15/188 |
| 2,044,428 | 6/1936 | Gilmer | 15/227 |
| 2,121,701 | 6/1938 | Landers | 15/227 |
| 2,127,904 * | 8/1938 | Arms | 401/201 |
| 2,157,543 | 5/1939 | Kingman | 91/54.7 |
| 2,165,420 | 7/1939 | Seifert | 15/210 |
| 2,187,163 | 1/1940 | Langer | 132/78.5 |
| 2,190,376 | 2/1940 | Daley | 132/78.5 |
| 2,319,873 | 5/1943 | Linz | 15/244 |
| 2,390,921 | 12/1945 | Clark | 15/104 |
| 2,419,896 | 4/1947 | Hobelmann | 15/227 |
| 2,528,812 | 11/1950 | Berman | 15/209 |
| 2,576,834 | 11/1951 | Hensgen | 99/179 |
| 2,835,911 | 5/1958 | Mahmarian | 15/131 |
| 2,878,967 | 3/1959 | Duke | 222/107 |
| 2,932,841 | 4/1960 | Graves | 15/209 |
| 3,006,023 | 10/1961 | Worthington | 15/506 |
| 3,007,192 * | 11/1961 | Quoss | 401/196 |
| 3,053,385 | 9/1962 | Spees | 206/63.2 |
| 3,143,276 | 8/1964 | Nichols | 229/55 |
| 3,214,783 | 11/1965 | Perry et al. | 15/143 |
| 3,369,267 | 2/1968 | Friedland et al. | 15/104.94 |
| 3,369,709 | 2/1968 | Clauss | 222/107 |
| 3,386,793 | 6/1968 | Stanton . | |
| 3,472,675 | 10/1969 | Gordon et al. | 117/36.9 |
| 3,491,396 | 1/1970 | Eannarino et al. | 15/104.94 |
| 3,630,346 | 12/1971 | Burnside | 206/56 AB |
| 3,647,305 | 3/1972 | Baker et al. | 401/7 |
| 3,707,012 | 12/1972 | Lane | 15/104.93 |
| 3,806,260 | 4/1974 | Miller | 401/7 |
| 3,826,259 | 7/1974 | Bailey | 128/269 |
| 3,899,080 | 8/1975 | Brunda | 206/531 |
| 3,969,026 * | 7/1976 | Johnson | 401/196 |
| 4,007,838 | 2/1977 | Awad | 206/484 |
| 4,111,666 | 9/1978 | Kalbow | 51/295 |
| 4,127,339 | 11/1978 | Malacheski et al. | 401/132 |
| 4,142,334 | 3/1979 | Kirsch et al. | 51/395 |
| 4,304,562 | 12/1981 | Bolan et al. | 8/137 |
| 4,420,080 | 12/1983 | Nakamura | 206/449 |
| 4,422,546 | 12/1983 | Charity | 206/77.1 |
| 4,515,703 | 5/1985 | Haq | 252/92 |
| 4,596,481 | 6/1986 | Tanaka | 401/132 |
| 4,627,129 | 12/1986 | Wittes | 15/244 C |
| 4,643,725 | 2/1987 | Schlesser et al. | 604/306 |
| 4,665,580 | 5/1987 | Morris | 15/118 |
| 4,683,001 | 7/1987 | Floyd et al. | 106/3 |
| 4,706,693 | 11/1987 | Spector | 132/79 R |
| 4,735,335 | 4/1988 | Torterotot | 220/270 |
| 4,738,887 | 4/1988 | Govertsen | 428/133 |
| 4,739,879 | 4/1988 | Nakamura | 206/205 |
| 4,751,934 | 6/1988 | Moir et al. | 132/79 D |
| 4,762,124 | 8/1988 | Kerch et al. | 128/156 |
| 4,776,356 | 10/1988 | Jou et al. | 15/244.4 |
| 4,787,374 | 11/1988 | DeYarman | 128/65 |
| 4,840,270 | 6/1989 | Caputo et al. | 206/205 |
| 4,913,307 | 4/1990 | Takata et al. | 220/276 |
| 4,963,045 | 10/1990 | Wilcox | 401/132 |
| 4,995,408 | 2/1991 | Wallschlaeger | 132/320 |
| 5,123,431 | 6/1992 | Wilson | 132/320 |
| 5,123,764 * | 6/1992 | Duncan et al. | 401/196 |
| 5,125,529 | 6/1992 | Torterotot | 220/270 |
| 5,161,688 | 11/1992 | Muchin . | |
| 5,263,609 | 11/1993 | Hoshino | 222/92 |
| 5,373,966 | 12/1994 | O'Reilly et al. | 222/94 |
| 5,380,110 | 1/1995 | Festa | 401/132 |
| 5,401,113 | 3/1995 | Gueret | 401/208 |
| 5,434,194 | 7/1995 | Fujimoto et al. | 521/134 |
| 5,487,932 | 1/1996 | Dunshee | 428/68 |
| 5,562,112 | 10/1996 | Gunderman et al. | 132/333 |
| 5,647,941 | 7/1997 | Gunderman et al. | 156/277 |
| 5,904,151 * | 5/1999 | Gueret | 401/266 |

\* cited by examiner

APPLICATOR FOR APPLYING AND DISTRIBUTING SUBSTANCES TO TARGET SURFACES

FIELD OF THE INVENTION

The present invention relates to applicators for use in manually applying coatings of a substance onto a desired target surface. More particularly, the present invention relates to such applicators which provide both dispensing and distribution functionality and therefore enhanced product performance.

BACKGROUND OF THE INVENTION

There are many types of topical products that are commercially available and/or commonly applied to a desired (target) surface in the form of a thin film or coating to protect, treat, modify, etc. the target surface. Such products include those in the skin care, cosmetics, pharmaceutical, and other personal care arenas. One common example of such a product is the antiperspirantldeodorant type of product, many of which are formulated as sprays, roll-on liquids, gels, creams, or solid sticks, and comprise an astringent material, e.g. zirconium or aluminum salts, incorporated into a suitable topical carrier. These products are designed to provide effective perspiration and odor control while also being cosmetically acceptable during and after application onto the axillary area or other areas of the skin.

Examples of suitable perforated caps or other shear force delivery means for use with such packaged compositions include those known in the art for application of creams, or those delivery means that are otherwise effective for delivering the composition of the present invention to the skin, with the resulting rheology of the extruded product preferably falling within the ranges described hereinabove for extruded compositions. Some examples of such perforated caps or other shear force delivery means, and some dispensing packages for use with compositions herein, are described in U.S. Pat. No. 5,000,356, issued to Johnson et al. on Mar. 19, 1991, which description is incorporated herein by reference.

While such delivery means have proven successful in applying such substances, in many instances a comparatively complex supply mechanism is required in order to dispense the product for application by shear force delivery means. This in turn typically requires a comparatively large canister to house not only the desired quantity of product but also the product retention and supply mechanism as well. Economic factors also typically require even travel size canisters for both elevator-type and push-up-stick packages to have considerable weight and occupy considerable volume, thus limiting the ability of the consumer to readily transport such devices. Moreover, such constructions for all practical considerations preclude the carrying of such devices on one's person such as in a pocket or modest-sized purse for replenishment of one's antiperspirant or deodorant during the course of an extended stay away from home.

Accordingly, it would be desirable to provide a discrete, convenient hand-held applicator for applying substances to target surfaces.

It would also be desirable to provide such an applicator which provides for a substantially uniform coating of such substances to yield enhanced product performance.

It would also be desirable to provide such an applicator which is easy to use and may be economically produced.

SUMMARY OF THE INVENTION

The present invention provides an applicator for applying and distributing a substance onto a target surface. The applicator comprises a substantially planar sheet of compressible, conformable material having opposed first and second surfaces and an interior region between said first and second surfaces. The sheet of material has a thickness between the first and second surfaces which decreases when the sheet of material is subjected to an externally-applied force in a direction substantially normal to the first surface. The applicator further includes at least one discrete reservoir extending inwardly of the first surface into the interior of the sheet of material which is at least partially filled with a substance and at least one discrete aperture formed in the first surface which is in fluid communication with the reservoir. Compression of the sheet of material via an externally-applied force substantially normal to said first surface expresses product from the aperture and translational motion of the first surface relative to a target surface applies and distributes said product onto the target surface. In a preferred embodiment, a plurality of apertures are associated with corresponding reservoirs forming a delivery zone near one end of a hand-held applicator, and the sheet material is preferably resilient both in compression and in bending to conform to irregular target surfaces. A wide variety of substances are contemplated, including particularly antiperspirant/deodorant products. Other embodiments include a single reservoir feeding multiple apertures.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify like elements and wherein:

DETAILED DESCRIPTION OF THE INVENTION

1. Applicator Construction.

Figure 1:
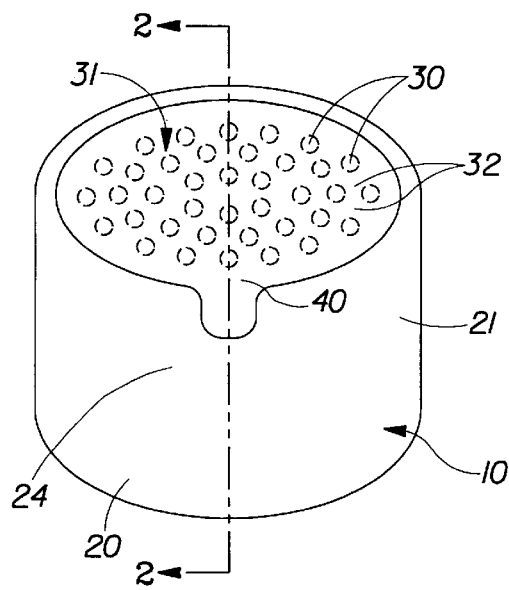
FIG. 1 is a plan view of a preferred embodiment of an applicator in accordance with the present invention.

FIG. 1 depicts a preferred embodiment of an applicator 10 in accordance with the present invention. Applicator 10 comprises a substantially planar sheet of material 20 having a first side 21 and a second side 22, with the first and second sides defming an interior region 23 of the material 20. The first side 21 includes at least one aperture 30, and preferably a plurality of apertures 30 forming a delivery zone 31. The delivery zone 31 encompasses not only the apertures 30 but also the interstitial spaces 32 between adjacent apertures 30. As will be explained hereafter, the presence and construction of the interstitial spaces 32 are believed to play an important role in the distribution performance of the applicator 10 and in turn the performance of the substance distributed. In the embodiment shown in FIG. 1, the applicator 10 also includes an optional cover 40 releasably affixed to first side 21 so as to sealingly engage the first surface over and around the apertures 30 to occlude the apertures 30 and prevent premature dispensing or contamination of the product before the intended use. The cover may engage the first surface around the periphery of individual apertures or around the periphery of the delivery zone 31. Optional cover 40 may comprise a label with instructions or other suitable indicia thereon.

Second side 22 is preferably free of apertures and is preferably substantially planar, although for some applications it may be desirable to include some surface topography (such as a series of small protrusions coinciding with the locations of reservoirs 50) at least in the region underlying the delivery zone 31, to aid the user in orienting the applicator properly. The first surface also preferably includes a optional grasping portion 24 which is substantially free of apertures and is preferably located adjacent to one edge of the applicator. For some application configurations, it may be desirable to include a second delivery zone remotely from the first delivery zone, either elsewhere on the first surface or on the second surface of the applicator.

Figure 2:
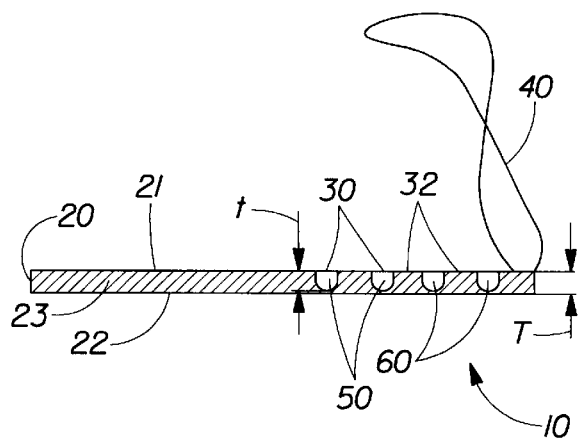
FIG. 2 is an elevational sectional view of the applicator of FIG. 1 taken along section line 2—2.

As shown more clearly in FIG. 2, the apertures 30 each extend inwardly of the first surface 21 into the interior 23 of the sheet of material 20 to form corresponding reservoirs 50 to contain a substance 60 prior to use. Suitable substances for use with the applicators of the present invention will be described in greater detail hereafter. Multiple substances may be employed in separate apertures and/or reservoirs, such that they remain segregated prior to applicator use but are co-mingled during use. This may be particularly useful wherein it is desired to prevent reactions between components prior to use and corresponding degradation or exhaustion of the active ingredients. Also, it may be desirable to include one or more "empty" apertures/reservoirs to either add air to the dispensed product and/or to act as a receiving reservoir to remove excess product from the target surface.

FIG. 2 also illustrates the geometrical relationship between the apertures 30, reservoirs 50, interstitial spaces 32, and the sheet material 20. The apertures, which may be of any desired size and shape, each have a peripheral edge which lies in the plane of the first surface 21 and defines the boundary of the aperture. In the instance where the sheet of material comprises a cellular structure, the apertures are substantially larger than the average cell size of the material. The interstitial spaces 32 are thus defined as the portion of the first surface 21 located between the peripheral edges of adjacent apertures. The reservoirs are located inwardly of the apertures and comprises a void within the interior of the sheet material. As with the apertures, the reservoirs are substantially larger than the average cell size of the material when the sheet of material is formed from a cellular structure. The reservoirs may or may not have the same cross-sectional shape in a direction parallel to the first surface 21 as that of the apertures 30. The sheet of material has an overall thickness T which is defined as the average distance between the opposing first and second surfaces 21 and 22 measured in a direction substantially normal to the first surface. In the instance wherein the surfaces are parallel, the thickness T is perpendicular to both surfaces, and where non-planar surfaces are involved the planes of respective surfaces are defined as an average position of a representative plane passing through the surface topography.

The use of one or more discrete reservoirs as opposed to a generally porous substance-impregnated material, provides a more controlled dosing functionality for the applicators of the present invention. The reservoir geometry and volume may be designed as desired for ultimate capacity and also rate of delivery, whether in the preferred pre-loaded configuration where the applicator is manufactured and sold with the product included or where the applicator is manufactured independently of the product and the consumer applies the substance to the applicator.

In a given applicator, the delivery zone may include a plurality of apertures having differing sizes and/or shapes in either a regular pattern or an irregular pattern, and reservoirs need not also be filled to the same level or have the same capacity. Apertures can be of any desired cross-sectional shape at their intersection with the first surface, such as oval, elliptical, hexagonal, etc, but a circular cross-sectional shape is presently preferred.

The reservoirs 50 extend inwardly from the first surface to a depth t. Accordingly, since the reservoirs are formed as voids in the sheet of material 20, the material is a comparatively thick material on the order of at least about 0.063–0.250 inches as compared to forming reservoirs in thin embossed materials such as polymeric films. The sheet of material 20 is formed from a material which is sufficiently conformable to enable the first surface 21 to conform to irregular target surfaces, and is preferably resiliently conformable for application in a dynamic environment as the first surface passes over non-planar and irregular surfaces. The material utilized for the applicator is also deformable in the direction of thickness T to supply and deliver the substance 60 to the target surface for application and distribution. Deformation of the sheet of material 20 in such a manner effectively reduces the volume of the reservoirs 50 in the region of deformation, thus expressing the substance from the reservoirs outwardly through the apertures 30 into contact with the target surface.

Compressive deformation in the context of the present invention, as described herein, is defined as a reduction in the dimension T of the material by application of an external force (or otherwise) such that the first and second surfaces become closer together and the interior dimension between them becomes smaller. This is to be distinguished from other types of deformable structures wherein surfaces of the material or structure are translated or rotated relative to each other to reduce the effective thickness of the material. Such a thickness may be more appropriately characterized as "caliper" rather than "thickness", as the "caliper" of such a material will be by definition greater than the "thickness" of the material from which it is made. An example of such a structure would be a three-dimensionally-embossed film which has a plurality of dimples or ribs formed therein. The film initially has a certain thickness or gauge, but after deformation out of the plane of the material the film has a caliper increase due to the dimensions of the ribs or dimples. Such a material may undergo a dimensional reduction in a plane normal to the plane of the material, but only via the deformation or destruction of the out-of-plane surfaces and structures. In structures and materials of the present invention, the caliper and thickness are substantially equivalent dimensions as any deviations from surface planarity in the vicinity of the delivery zone are insignificant. Accordingly, as the material itself compresses under the influence of an external force the first and second surfaces move toward one another without rotating or otherwise distorting the geometry of the sheet material.

Figure 3:
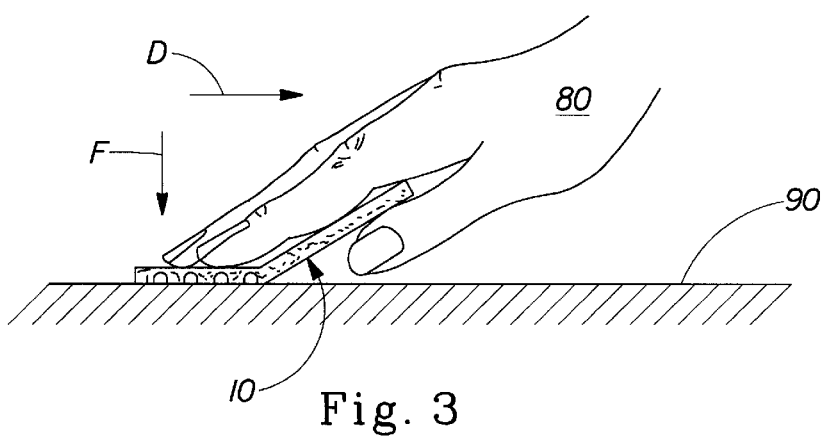
FIG. 3 is a schematical illustration of the applicator of FIGS. 1 and 2 being utilized to manually apply a coating of a substance to a target surface.

Without wishing to be bound by theory, it is believed that the use of a comparatively thick substantially planar material with reservoirs formed into the material rather than the use of a comparatively thin material which is formed into a non-planar structure provides an applicator which allows application forces to be more uniformly transferred to the target surface for a more uniform substance distribution. This is particularly important when the applied forces may be more discretely applied, such as by one or more fingers spaced apart, as for most scenarios it is desired to not have the resulting product distribution mirror the pattern of the applied forces. For example; if one holds the applicator pad as shown in FIG. 3 it is desired to form a substantially uniform coating of the substance upon the target surface rather than four streaks of product corresponding to the location of the four fingers.

Another important characteristic for applicators of the present invention is the ability of the material to "glide" across the target surface without rolling up or otherwise becoming distorted. This also helps to ensure a comparatively even substance distribution on the target surface. Accordingly, selection of suitable applicator materials should account for not only the substance characteristics in terms of shear and other properties, but also the coefficient of friction of the material and the target surface.

The sheet material 20 may be unitary in nature, constructed from a single monolithic piece of material, or may comprise two or more layers or plies of material. In addition, it may be desirable to form the apertures and reservoirs in one layer of material, completely penetrating the sheet of material, and then laminating another layer of similar or diverse composition onto the second surface of the first piece of material to close the inward end of the reservoirs.

A presently preferred construction utilizes a polyethylene/EVA foam pad with multiple heat-embossed product reservoirs/apertures in one surface. However, a wide variety of other materials are contemplated as being within the scope of the present invention having suitable physical and/or chemical properties for the intended substance and intended target surface. The foam pad may be cut to the desired shape with a press and rule die, or other suitable means. The substance may be injected, doctored, or otherwise supplied to the reservoirs. The applicator may be of any desired size and shape, although the shape depicted in FIGS. 1–3 in dimensions of approximately 2.7"×2.4"×0.125" thick has proven satisfactory in use, with 38 equally sized and spaced reservoirs forming an ellipse having an approximate major dimension of about 1.5 to 2.0 inches and a minor dimension of about 0.9 to 1.3 inches and delivering approximately 0.4 grams of antiperspirant composition (such as that described below). A presently preferred aperture size is between about 0.100 and about 0.150 inches in diameter, with a circular cross-section, an edge-to-edge spacing of between about 0.050 and about 0.110 inches, with a substantially straight-walled reservoir of similar cross-section extending inwardly therefrom.

Figure 6:
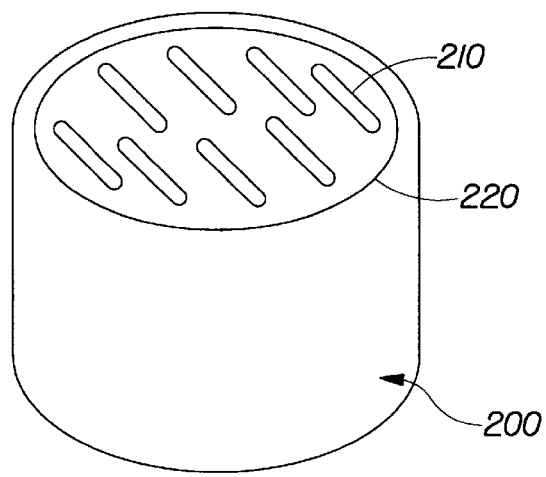
FIG. 6 is a plan view of another preferred embodiment of an applicator in accordance with the present invention.

FIG. 6 depicts another embodiment of the present invention in the form of an applicator 200 having dimensions of approximately 2.7"×2.4"×0.125" thick, which has proven satisfactory in use. Applicator 200 has 8 equally sized and spaced slot type reservoirs 210 positioned diagonally at 45° within an ellipse area 220 having an approximate major dimension of about 1.5 to 2.0 inches and a minor dimension of about 0.9 to 1.3 inches and delivering approximately 0.4 grams of antiperspirant composition (such as that described below). A presently preferred slot type reservoir 210 for applicator 200 has a length between about 0.578 and about 0.473 inches, a width between about 0.100 and about 0.080 inches, with a slot type cross-section with rounded ends, an edge-to-edge spacing between reservoirs 210 of between about 0.220 and about 0.080 inches, with a substantially straight-walled reservoir of similar cross-section extending inwardly therefrom between about 0.125 and about 0.080 inches in depth.

Figure 7:
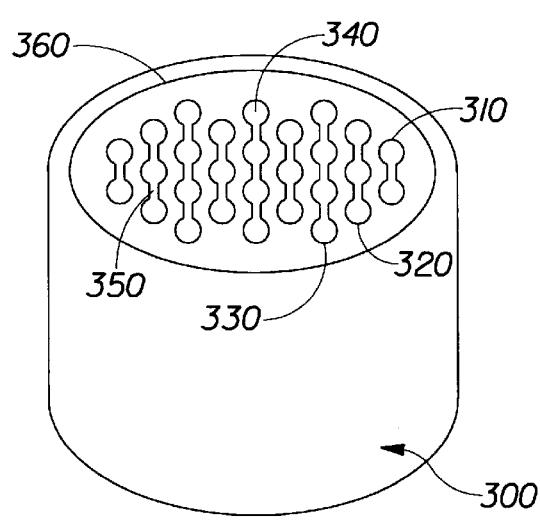
FIG. 7 is a plan view of another preferred embodiment of an applicator in accordance with the present invention.

FIG. 7 depicts another embodiment of the present invention in the form of an applicator 300 having dimensions of approximately 2.7"×2.4"×0.125" thick, which has proven satisfactory in use. Applicator 300 has 9 aperture-channel type reservoirs of varying configuration positioned within an ellipse area 360 having an approximate major dimension of about 1.5 to 2.0 inches and a minor dimension of about 0.9 to 1.3 inches and delivering approximately 0.4 grams of antiperspirant composition (such as that described below). Applicator 300 has a variation of: 2-aperture-channel reservoirs 310 having two apertures 340 connected by a single channel 350, 3-aperture-channel reservoirs 320 having three apertures 340 connected by two channels 350, and 4-aperture-channel reservoirs 330 having four apertures 340 connected by three channels 350. A presently preferred aperture 340 is between about 0.165 and about 0.135 inches in diameter, with a circular cross-section. A presently preferred channel 350 is between about 0.055 and about 0.045 inches in width, with a rectangular cross-section. A presently preferred spacing between the center of adjoining apertures 340 is between about 0.280 and about 0.200 inches in length. Edge-to-edge spacing between the apertures 340 is between about 0.095 and about 0.065 inches. Reservoirs are substantially straight-walled of similar cross-section extending inwardly therefrom between about 0.125 and about 0.080 inches in depth.

Figure 8:
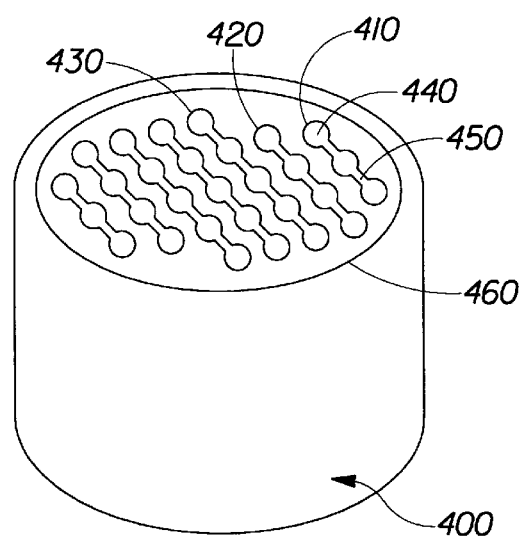
FIG. 8 is a plan view of another preferred embodiment of an applicator in accordance with the present invention.

FIG. 8 depicts another embodiment of the present invention in the form of an applicator 400 having dimensions of approximately 2.7"×2.4"×0.125" thick, which has proven satisfactory in use. Applicator 400 has 7 aperture-channel type reservoirs of varying configuration positioned diagonally at 45° within an ellipse area having an approximate major dimension of about 1.5 to 2.0 inches and a minor dimension of about 0.9 to 1.3 inches and delivering approximately 0.4 grams of antiperspirant composition (such as that described below). Applicator 400 has a variation of: 3-aperture-channel reservoirs 410 having three apertures 440 connected by two channels 450, 4-aperture-channel reservoirs 420 having four apertures 440 connected by three channels 450, and 5-aperture-channel reservoirs 430 having five apertures 440 connected by four channels 450. A presently preferred aperture 440 is between about 0.165 and about 0.135 inches in diameter, with a circular cross-section. A presently preferred channel 450 is between about 0.055 and about 0.045 inches in width, with a rectangular cross-section. A presently preferred spacing between the center of adjoining apertures 440 is between about 0.280 and about 0.200 inches in length. Edge-to-edge spacing between the apertures 440 is between about 0.095 and about 0.065 inches. Reservoirs are substantially straight-walled of similar cross-section extending inwardly therefrom between about 0.125 and about 0.080 inches in depth.

For a given product, an applicator design should be optimized to minimize premature dispensing and to maximize intentional-delivery of the desired product. A method which is believed to prevent premature dispensing of the desired product is to maximize the surface area of the reservoirs to which the product will adhere. The product typically has an affinity to the applicator surface; therefore, the product has a tendency to remain within the reservoirs. However, increasing the surface area of the reservoirs also decreases the amount of product that will be delivered intentionally later by the consumer. The propensity of the product to stay in the reservoir due to reservoir surface area, and the corresponding propensity of the product to be intentionally delivered by the consumer, are inversely related but not necessarily linearly proportional. Without wishing to be bound by theory, it is believed that as the surface area of a reservoir is increased for a constant reservoir volume and depth, there results a reduction in premature dispensing but also a corresponding, but not necessarily linearly, proportional reduction in intentionally-delivered product. Such theory may be discussed in reference to an aspect ratio defined and calculated as the [surface area of the reservoir]/[surface area of a cylindrical reservoir having an equal volume and depth]. It is believed that as the aspect ratio is increased, there results a reduction in premature dispensing but also a corresponding, but not necessarily linearly, proportional reduction in intentionally-delivered product. In determining the optimal applicator design for a given product, this aspect ratio may be used to compare various designs. For the embodiments illustrated in FIGS. 6, 7, and 8 such a method of optimization was utilized and it was found that an aspect ratio ranging from about 1 to about 5 has proven satisfactory in use for the products described herein.

As mentioned previously, it is presently preferred that the materials utilized in the present invention are not only compressible in the thickness direction but also conformable in the planar direction so as to accommodate various target surface topographies in use. It is also preferred that suitable sheet materials also be resilient, preferably both in terms of their compressibility and in terms of their bending conformability. Resilience is defined consistent with its everyday meaning, as evidenced by *Webster's Ninth New Collegiate Dictionary*, as "the capability of a strained body to recover its size and shape after deformation caused esp. by compressive stress." Resilience of the material causes it to tend to return to its undeformed, preferably substantially planar state and original thickness after compressive or bending forces, thereby enabling it to conform to various target surfaces and yet maintain target surface contact for proper substance distribution.

Preferred material properties, as well as the properties of the presently preferred material, Volara 2E0 ⅛" PE/EVA polyethylene/ethylene vinyl acetate copolymer (12%VA) fine-cell crosslinked polymer foam, commercially available from Voltek, 100 Shepard Street, Lawrence, Mass. 01843, are presented in the table below:

| PROPERTIES | Volara 2E0 ⅛" | Preferred Range | Test Method |
|---|---|---|---|
| Thickness in. | 0.125 | 0.063–0.250 | ASTM D-3575 |
| Density lbs/cu ft. | 2 nominal | 2–6 | ASTM D-3575 |
| Tensile Str psi (MD) | 55 min. | 40–200 | ASTM D-3575 |
| Break Elongation % (MD) | 140 min. | 100–350 | ASTM D-3575 |
| Tear Resistance lb/in (MD) | 7 min. | 4.5–30 | ASTM D-3575 |
| Compression Str. Psi | | | |
| @25% deflection | 2.5 min. | 1.5–15 | ASTM D-3575 |
| @50% deflection | 9 min. | 4–25 | ASTM D-3575 |
| Compression set % | 30 max. | 0–50 | ASTM D-3575 |

To quantify stiffniess, a suitable method is TAPPI T489 om-92, Stiffiess of paper and paperboard (Taber-type stiffness tester). Results are in gram centimeters or Taber units. Equipment used; Taber V-5 model 150B Stifffiess Tester.

Note: NO weight added and results measured at 15 degrees displacement.

| | Actual Data: | |
|---|---|---|
| Material ⅛" caliper (Voltek #) | MD | CD |
| polyethylene (2A) | 65 gm cm | 2 |
| PE/EVA 12% VA (2EO) | 47 | 34 |
| PE/EVA 18% VA (2G) | 41 | 32 |

Preferred limit range for ⅛" thick, 2PCF foam are: MD testing=75–35 gram centimeters, CD testing=50–25 gram centimeters While Volara 2EO is presently preferred material, alternate Volara grades and alternate foam materials such as open cell foam, non-crosslinked foam, foam with a range of cell sizes, alternate resins, 100% polyethylene, polystyrene, polypropylene, rubber, urethanes, other ethylene copolymers, propylene copolymers, and other synthetic materials having similar material properties could be used. Note, however, for some applications materials being substantially stiffer or softer may be preferred.

In the embodiment shown in FIGS. 1 and 2, the reservoirs have walls which are substantially normal to the first surface of the sheet of material. However, for certain product formulations of the substance to be delivered to the target surface it may be desirable to provide reservoir and aperture geometries wherein the reservoirs have sidewalls at angles other than 90 degrees, such as, for example, fuinnel-shaped tapered aperture/reservoir geometries wherein the reservoir narrows with increasing distance inwardly from the first surface or "undercut" aperture geometries where the reservoir widens with increasing distance inwardly from the first surface. Reservoirs may also be formed with substantially planar bottoms (the portion located distally from the apertures and within the interior of the sheet of material), or the bottoms of the reservoirs may be radiused, depending upon the manufacturing method of choice and the nature of the substances and sheet materials employed.

In addition, it is preferred that when the sheet of material comprises a porous material the reservoirs include some suitable means of preventing substance migration into the matrix of the sheet material. A presently preferred method of preventing such migration is to utilize a closed-cell foam material. However, such means may include an impermeable coating or may be some other means of rendering the reservoir walls impermeable such as thermally melting the porous sheet material during formation of the apertures and reservoirs to form a "skin". Additional layers or coatings of polymers such as PET, nylon, etc. may be employed on the reservoir walls, the second side 21 of the applicator, or other regions where it is desired to limit substance penetration of the material. Any such treatments or approaches would be tailored to suit the particular combination of substance and applicator material(s). For some applications, it may also be desirable that the inner surfaces of the reservoir(s) and aperture(s) have some degree of surface topography to aid in anchoring the substance. Internal structures such as protrusions, "bosses", peripheral rings, etc., may also be desirable to aid in substance retention. Various reservoir configurations may be employed without being limited to the aperture shape or the overall shape of the applicator, and may be tailored as desired to facilitate substance retention and/or dispensing.

FIG. 3 provides an illustration of an applicator 10 in accordance with the present invention being utilized to apply a substance to a target surface. As shown in FIG. 3, the applicator 10 is manually grasped by the hand 80 of a user, typically by pinching the applicator between the thumb and palm with the fmgers contacting the second surface 22 in the vicinity of apertures 30 and the thumb contacting the grasping portion 24. The user then brings the delivery zone 31 of the applicator 10 into contact with a target surface 90, which may have any surface topography and may be planar or non-planar, and applies a force having at least a normal force vector component in a direction F which is substantially normal to the target surface 90. A tangential force or force vector component exerted in direction D is applied, preferably simultaneously with the application of normal force F, to move the applicator across the target surface 90 to apply a substantially uniform coating of the substance 60 to the target surface, preferably in a region substantially conforming to the scope of the delivery zone 31 and to the distance travelled. The normal and tangential forces may combine in such a manner as to define a total force vector which defines an angle between about 0 and about 90 degrees from the plane of the first surface. Such a manner of application provides for dispensing of the substance during the distribution phase of the process, rather than the typical extrusion or dispensing of substances followed by the distribution phase.

In a dynamic application environment such as that depicted in FIG. 3, in contrast with a "static" application scenario with no relative translational movement, it is believed that the relationship between the apertures (where a plurality are utilized) and the spaces between them is an important consideration in the design of suitable applicator geometries for particular substances. Each aperture has a peripheral edge which is surrounded by a portion of the first surface of the sheet material. As the sheet material, at least the first surface thereof, is preferably substantially planar, each aperture is thus surrounded by a substantially planar ring of material which contacts the target surface around the aperture and which provides a "rub-in" surface to distribute the substance on the target surface. Where the substance is or becomes flowable at the time of application, this ring of material forms a gasket-like surface which aids in uniformly distributing product by encouraging the outward flow of product from the apertures. Optionally, if desired a certain amount of surface texture, such as microtexture, may be applied to the portions of the first surface between and/or adjacent to the apertures to aid in the distribution function and/or the aesthetics of the application function in terms of skin feel, etc.

Figure 4:
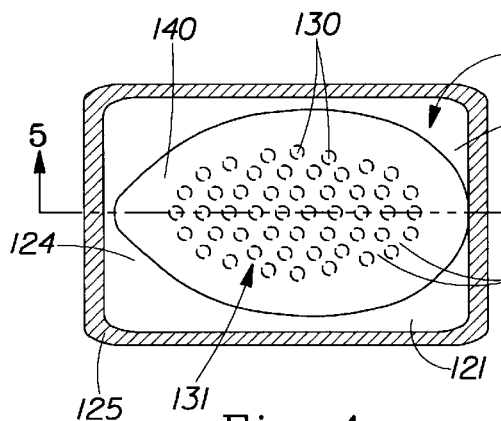
FIG. 4 is a plan view similar to FIG. 1 of another embodiment of an applicator.
Figure 5:
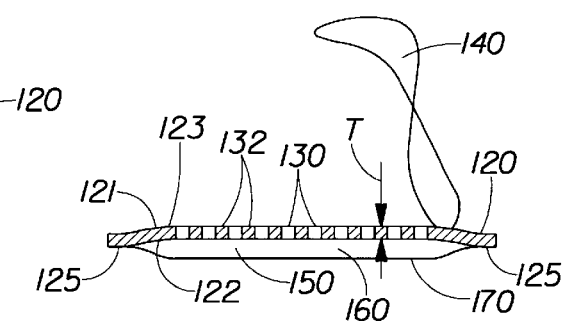
FIG. 5 is an elevational sectional view similar to FIG. 2 of the applicator of FIG. 4 taken along section line 5—5.

The applicators of the present invention depicted in FIGS. 1–3 have corresponding plural apertures and plural reservoirs, and preferably a 1:1 ratio of apertures to reservoirs. However, other combinations of apertures and reservoirs are also possible, such as multiple reservoirs supplying each aperture or multiple apertures supplied by a single reservoir. FIGS. 4 and 5 depict such an alternate embodiment. The applicator 110 of FIGS. 4 and 5 has a sheet of material 120 similar to the sheet of material 20 of FIGS. 1–3, but unlike the applicator 10 the applicator 110 has a plurality of apertures 130 which extend inwardly from the first surface 121 through the interior 123 of the sheet of material all the way through the second side 122, such that a completely unobstructed passageway is provided through the sheet of material 120. In such an embodiment, the sheet of material has a thickness T which is equivalent to the distance t (omitted for clarity). The apertures 130 form a delivery zone 131, are separated by interstitial spaces 132, and are preferably but optionally covered by a removable cover 140 which may have instructions or other suitable indicia thereon. The applicator 110 also includes a backing sheet 170 which is peripherally joined to the sheet of material 120 via a heat seal 125 or other suitable sealing technique, the backing sheet 170 cooperating with the seal 125, sheet of material 120, and cover 140 to form at least one, and preferably only one, reservoir 150 for containing a product 160 therein.

Another variation would include the use of a single large reservoir in an embodiment similar to that of FIG. 1, but including a plurality of "islands" protruding from the floor of the reservoir to provide a surface-contacting rub-in surface analogous to the network of interstitial spaces formed between multiple discrete apertures as shown in FIG. 1.

The apertures of the applicators of the present invention may be sealed prior to use in other ways than the use of a cover/label such as cover 40/140. For example, applicators may be sealed/bonded to one another in face-to-face or back-to-back relationship such that one surface of one applicator obstructs the apertures of the next. Other possible orientations include face-to-face orientations with delivery zones non-aligned and overlying other portions of the first surface, face-to-back, etc., and pairs of such materials can be packaged in a barrier film (foil laminate, metallized polyester, etc.) to form a convenient package.

The applicator of the present invention comprises a packaged delivery system having a shear force delivery means. Other examples of such delivery systems are well known in the art, and typically comprise an enclosed package or container having an attached shear force delivery means such as a perforated cap or other perforated surface. Shear force delivery means subject the delivered substance to shear forces which counteract the tendencies of the substance to agglomerate and/or remain in comparatively large or thick deposits and spread across the target surface. The application of shear force in combination with the substance delivery process is particularly important when the rheology and other product characteristics change under the influence of shear forces, such as the substance becoming more flowable under shear. Additional discussion of substance rheology follows hereafter.

Typical shear force delivery means include any ridged or flexible surface, preferably a ridged surface, suitable for attachment to a package or other product, and which has a plurality of openings, apertures or orifices extending through the thickness of the ridged or flexible surface through which the composition can flow to the intended site of application. However, in accordance with the present invention the applicators described herein provide delivery and distribution functionality meeting or exceeding that of other shear force delivery means in a convenient, economical, easy-to-use form.

2. Representative Compositions.

In the present invention, the term "substance" can mean a flowable substance which is substantially non-flowing prior to delivery to a target surface. "Substance" can also mean a material which doesn't flow at all, such as a fibrous or other interlocking material. "Substance" may mean a fluid or a solid. "Substance" is defined in this invention as any material capable of being held in open three-dimensional recesses of the applicator material in the absence of external forces other than those of gravity. While substances which are substantially non-flowable prior to delivery are presently preferred, substances which are flowable or have greater flowability may be found suitable for use in the present invention wherein overwraps, seals, or the like provide for sufficient substance retention/protection prior to use.

Adhesives, electrostatics, mechanical interlocking, capillary attraction, surface adsorption, van der Waals forces, and friction, for example, may be used to hold the substances in the apertures and/or reservoirs. The substances are intended to be at least partially released therefrom when exposed to contact with external surfaces when the applicator is subjected to externally-applied compressive forces. Of current interest in the present invention include substances such as gels, pastes, creams, lotions, foams, powders, agglomerated particles, prills, microencapsulated liquids, waxes, suspensions, liquids, and combinations thereof.

The spaces in the three dimensional structure of the present invention are normally open; therefore it is desirable to have substances stay in place and not run out of the structure without an activation step. Accordingly, substances which are preferred are capable of staying within the apertures and/or reservoirs even in the absence of an overwrap. The activation step utilized in accordance with the present invention is deformation of the three dimensional structure by compression, which overcomes the tendencies of the substance to remain within the applicator.

Preferred substances include those which may be liberated from the applicator without the need for solvents (including water, etc.) in order to provide for a ready-to-use device. However, such preference should not preclude the use of otherwise suitable substances merely because some degree of solvent use may be necessary. Suitable substances may be anhydrous, and perform satisfactorily and desirably in the absence of water.

Antiperspirant/Deodorant Compositions

The antiperspirant and deodorant substances for use in the applicator of the present invention are non-flowing compositions which are intended for topical application to the underarm or other suitable areas of the skin. These deodorant and antiperspirant compositions comprise an active ingredient and a suspending or thickening agent incorporated into a suitable liquid carrier. In this context, the term "active" refers to antiperspirant actives, deodorant actives, or fragrances, and include any known or otherwise safe and effective antiperspirant, deodorant, or fragrance active material. The terms "antiperspirant active" and "deodorant active" specifically refers to topical materials which can prevent or eliminate malodors and/or perspiration wetness. The term "fragrance" as used herein specifically refers to any topical material which covers or masks malodors resulting from perspiration, or which otherwise provides the composition with the desired perfumed aroma.

Antiperspirant Active

The antiperspirant compositions for use in the applicator of the present invention comprise antiperspirant active suitable for application to human skin. The antiperspirant active may be solubilized in the antiperspirant compositions or may be suspended as an undissolved or precipitated solid. The concentration of the antiperspirant active in the antiperspirant compositions should be sufficient to provide the desired odor and wetness control from the antiperspirant composition selected.

The antiperspirant compositions described herein comprise antiperspirant active at concentrations of from about 0.5% to about 60%, preferably from about 0.5% to about 50%, more preferably from about 5% to about 35%, by weight of the selected antiperspirant composition. All such weight percentages are calculated on an anhydrous metal salt basis exclusive of water and any complexing agents such as glycine, glycine salts, or other complexing agents.

The antiperspirant active for use in the antiperspirant compositions described herein include any compound, composition or other material having antiperspirant activity. Preferred antiperspirant actives include the astringent metallic salts, especially the inorganic and organic salts of aluminum, zirconium and zinc, as well as mixtures thereof. Particularly preferred are the aluminum and zirconium salts, such as aluminum halides, aluminum hydroxyhalides, zirconyl oxyhalides, zirconyl hydroxyhalides, and mixtures thereof.

Preferred aluminum salts for use in the antiperspirant compositions include those which conform to the formula:

$$Al_2(OH)_a Cl_b \cdot x H_2O$$

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5, and "2/3 basic chlorhydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, which disclosures are incorporated herein by reference. Mixtures of aluminum salts are described in British Patent Specification 1,347,950, Shin et al., published Feb. 27, 1974, which description is also incorporated herein by reference.

Preferred zirconium salts for use in the antiperspirant compositions include those which conform to the formula:

$$ZrO(OH)_{2-a}Cl_a \cdot x H_2O$$

wherein a is any number having a value of from about 0 to about 2; x is from about 1 to about 7; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorhydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, which descriptions are incorporated herein by reference.

The antiperspirant active may be formulated as particulate solids in the form of dispersed solid particles having a preferred average particle size or diameter of less than about 100 μm, more preferably from about 2 μm to about 50 μm, even more preferably from about 0.4 μm to about 40 μm.

The antiperspirant compositions described herein may comprise solubilized antiperspirant active, preferably solubilized antiperspirant active in an anhydrous system. The concentration of solubilized antiperspirant active in the antiperspirant compositions preferably ranges from about 0.1% to 35%, more preferably from about 0.5% to about 25%, even more preferably from about 1% to about 17%, even more preferably from about 6% to about 17%, by weight of the selected antiperspirant composition (weight percentages calculated on an anhydrous metal salt basis exclusive of water and any complexing agents such as glycine, glycine salts, or other complexing agents).

Deodorant Active

The deodorant compositions for use in the applicator of the present invention comprise deodorant active at concentrations ranging from about 0.001% to about 50%, preferably from about 0.01% to about 20%, more preferably from about 0.1% to about 10%, even more preferably from about 0.1% to about 5%, by weight of the selected deodorant composition. These deodorant actives can include any known or otherwise safe and effective deodorant active suitable for topical application to human skin.

Deodorant actives suitable for use in the deodorant compositions described herein include any topical material that is known for or is otherwise effective in preventing or eliminating malodor associated with perspiration. These deodorant actives are typically antimicrobial agents (e.g., bacteriocides, fungicides), malodor-absorbing material, or combinations thereof.

Preferred deodorant actives are antimicrobial agents, non-limiting examples of which include cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichlorio-2'-hydroxy diphenyl ether (triclosan), 3,4, 4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

Other deodorant actives include odor-absorbing materials such as carbonate and bicarbonate salts, including alkali metal carbonates and bicarbonates, ammonium and tetraalkylammonium. Preferred are sodium and potassium salts of such odor-absorbing materials.

Fragrance

Fragrances suitable for use herein include any topical material that is known for or is otherwise effective in masking malodor associated with perspiration, or which otherwise provides the substance compositions with the desired perfumed aroma. These fragrances include any perfume or perfume chemical suitable for topical application to the skin. The fragrance material can be used alone or in combination with the antiperspirant active or deodorant active. Concentrations of the fragrance material generally range from about 0.001% to about 50%, preferably from about 0.01% to about 20%, more preferably from about 0.1% to about 10%, even more preferably from about 0.1% to about 5%, by weight of the selected antiperspirant or deodorant composition.

The concentration of the fragrance in the antiperspirant or deodorant compositions should be effective to provide the desired aroma characteristics or to mask malodor, wherein the malodor is inherently associated with the composition itself or is associated with malodor development from human perspiration. Also, the fragrance and whatever carriers accompany it should not impart excessive stinging to the skin, especially broken or irritated skin, at the levels previously disclosed. The fragrance will typically be in the form of water insoluble perfumes that are solubilized in the antiperspirant or deodorant compositions described herein.

Fragrances are made by those skilled in the art in a wide variety of fragrances and strengths. Typical fragrances are described in Arctander, Perfume and Flavour Chemicals (Aroma Chemicals), Vol. I and II (1969); and Arctander, Perfume and Flavour Materials of Natural Origin (1960). U.S. Pat. No. 4,322,308 and U.S. Pat. No. 4,304,679, both incorporated herein by reference, disclose fragrance components as generally including, but are not limited to, volatile phenolic substances (such as iso-amyl salicylate, benzyl salicylate, and thyme oil red); essence oils (such as geranium oil, patchouli oil, and petitgrain oil); citrus oils; extracts and resins (such as benzoin siam resinoid and opoponax resinoid); "synthetic" oils (such as Bergamot 37 and 430, Geranium 76 and Pomeransol 314); aldehydes and ketones (such as B-methyl naphthyl ketone, p-t-butyl-A-methyl hydrocinnamic aldehyde and p-t-amyl cyclohexanone); polycyclic compounds (such as coumarin and β-naphthyl methyl ether); esters (such as diethyl phthalate, phenylethyl phenylacetate, non-anolide-1:4). Fragrances also include esters and essential oils derived from floral materials and fruits, citrus oils, absolutes, aldehydes, resinoides, musk and other animal notes (e.g., natural isolates of civet, castoreum and musk), balsamic, etc. and alcohols (such as dimyrcetol, phenylethyl alcohol and tetrahydromuguol). Examples of such components useful as fragrances herein include decyl aldehyde, undecyl aldehyde, undecylenic aldehyde, lauric aldehyde, amyl cinnamic aldehyde, ethyl methyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor, para-hydroxy phenolbutanone, 6-acetyl 1,1,3,4,4,6 hexamethyl tetrahydronaphthalene, alpha-methyl ionone, gamma-methyl ionone, and amyl-cyclohexanone and mixtures of these components.

Other suitable fragrances are those which mask or help to mask odors associated with perspiration (hereinafter referred to as odor masking fragrances), some non-limiting examples of which are described in U.S. Pat. No. 5,554,588, U.S. Pat. No. 4,278,658, U.S. Pat. No. 5,501,805, and EP Patent Application 684 037 A1, all of which are incorporated herein by reference in their entirety. Preferred odor masking fragrances are those which have a Deodorant Value of at least about 0.25, more preferably from about 0.25 to about 3.5, even more preferably from about 0.9 to about 3.5, as measured by the Deodorant Value Test described in EP Patent Application 684 037 A1.

The fragrance for use herein may also contain solubilizers, diluents, or solvents which are well known in the art. Such materials are described in Arctander, Perfume and Flavour Chemicals (Aroma Chemicals), Vol. I and II (1969). These materials typically include small amounts of dipropylene glycol, diethylene glycol, $C_1$–$C_6$ alcohols, and/ or benzyl alcohol.

Suspending or Thickening Agent

The antiperspirant and deodorant compositions for use in the applicator of the present invention comprise a suspending or thickening agent to help provide the compositions with the desired viscosity or product hardness, or to otherwise help suspend any dispersed solids or liquids within the compositions. Suitable suspending or thickening agents include any material known or otherwise effective in providing suspending or thickening properties to the compositions, or which otherwise provide structure to the final product forms. These suspending or thickening agents include gelling agents, and polymeric or nonpolymeric or inorganic thickening or viscosifying agents. Such materials will most typically include organic solids, silicone solids, crystalline or other gellants, inorganic particulates such as clays or silicas, or combinations thereof.

The concentration and type of the suspending or thickening agent selected for use in the antiperspirant and deodorant compositions will vary depending upon the desired product form, viscosity, and hardness. For most suspending or thickening agents suitable for use in the compositions described herein, the concentration of such suspending or thickening agents will most typically range from about 0.1% to about 35%, more typically from about 0.1% to about 20%, by weight of the selected antiperspirant or deodorant composition.

Suitable gelling agents for use as suspending or thickening agents herein include, but are not limited to, fatty alcohols, esters of fatty alcohols, fatty acids, hydroxy fatty acids, esters and amides of fatty acids or hydroxy fatty acids, ethers of fatty acids, ethoxylated fatty alcohols, ethoxylated fatty acids, waxes, cholesterolic materials, dibenzylidene alditols, lanolinolic materials, other amide and polyamide gellants, and corresponding salts thereof. All such gellants preferably have a fatty alkyl moiety having from about 14 to about 60 carbon atoms, more preferably from about 20 to about 40 carbon atoms, and which may be saturated or unsaturated, substituted or unsubstituted, branched or linear or cyclic.

The term "substituted" as used herein refers to chemical moieties known or otherwise effective for attachment to gellants or other compounds. Such substituents include those listed and described in C. Hansch and A. Leo, *Substituent Constants for Correlation Analysis in Chemistry and Biology* (1979), which listing and description are incorporated herein by reference. Examples of such substituents include, but are not limited to, alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

The term "corresponding salts" as used herein refers to cationic salts formed at any acidic (e.g., carboxyl) group, or anionic salts formed at any basic (e.g., amino) group, either of which are suitable for topical application to human skin. Many such salts are known in the art, examples of which are described in World Patent Publication 87/05297, Johnston et al., published Sep. 11, 1987, which description is incorporated herein by reference.

Suitable fatty alcohols for use in the antiperspirant compositions described herein include those compounds that are solids under ambient conditions and that have from about 8 to about 40 carbon atoms. These gelling agents are wax-like materials which are most typically used at concentrations ranging from about 0.1% to about 25%, preferably from about 3% to about 20%, by weight of the selected antiperspirant composition. Specific examples of fatty alcohols for use herein include, but are not limited to, cetyl alcohol, myristyl alcohol, stearyl alcohol, and the Unilins available from Petrolite as Unilin 550, Unilin 700, Unilin 400, Unilin 350, and Unilin 325.

Nonlimiting examples of suitable esters of fatty alcohols for use in the antiperspirant compositions described herein include tri-isostearyl citrate, ethyleneglycol di-12-hydroxystearate, tristearylcitrate, stearyl octanoate, stearyl heptanoate, trilaurylcitrate.

Suitable fatty acids for use in the antiperspirant and deodorant compositions described herein include, but are not limited to, fatty acid and hydroxy or alpha hydroxy fatty acids having from about 10 to about 40 carbon atoms, examples of which include 12-hydroxystearic acid, 12-hydroxylauric acid, 16-hydroxyhexadecanoic acid, behenic acid, eurcic acid, stearic acid, caprylic acid, lauric acid, isostearic acid, combinations thereof, and salts thereof.

Some preferred examples of fatty acids suitable for use herein are disclosed in U.S. Pat. No. 5,429,816, issued to Hofrichter et al. on Jul. 4, 1995; and U.S. Pat. No. 5,552,136, issued to Motley on Sep. 3, 1996, both disclosures of which are incorporated by reference herein. Some commercial examples of fatty acids include, but are not limited to, Unicid 400, available from Petrolite.

Nonlimting examples of salts of fatty acids for use in the antiperspirant and deodorant compositions described herein include those compounds wherein the fatty acid moiety has from about 12 to about 40 carbon atoms, preferably from about 12 to about 22 carbon atoms, more preferably from about 16 to about 20 carbon atoms, most preferably about 18 carbon atoms. Suitable salt forming cations for use with these gelling agents include metal salts such as alkali metals, e.g. sodium and potassium, and alkaline earth metals, e.g. magnesium, and aluminum. Preferred are sodium and potassium salts, more preferably sodium stearate, sodium palmitate, potassium stearate, potassium palmitate, sodium myristate, aluminum monostearate, and combinations thereof. Most preferred is sodium stearate.

Suitable ethoxylated gellants for use in the antiperspirant compositions described herein include, but are not limited, Unithox 325, Unithox 400, Unithox 450, Unithox 480, Unithox 520, Unithox 550, Unithox 720, and Unithox 750 (all of which are available from Petrolite), C20 to C40 pareth-3, and combinations thereof.

Suitable fatty acid esters for use in the antiperspirant compositions described herein include ester waxes, monoglycerides, diglycerides, triglycerides and combinations thereof. Preferred are the glyceride esters. Nonlimiting examples of suitable ester waxes including stearyl stearate, stearyl behenate, palmityl stearate, stearyl octyldodecanol, cetyl esters, cetearyl behenate, behenyl behenate, ethylene glycol distearate, ethylene glycol dipalmitate, and beeswax. Examples of commercial ester waxes include Kester waxes from Koster Keunen, Crodamol SS from Croda, and Demalcare SPS from Rhone Poulenc. Preferred are glyceryl tribehenate and other triglycerides, wherein at least about 75%, preferably about 100%, of the esterified fatty acid moieties of said other triglycerides each have from about 18 to about 36 carbon atoms, and wherein the molar ratio of glyceryl tribehenate to said other triglycerides is from about 20:1 to about 1:1, preferably from about 10:1 to about 3:1, more preferably from about 6:1 to about 4:1. The esterified fatty acid moieties may be saturated or unsaturated, substituted or unsubstituted, linear or branched, but are preferably linear, saturated, unsubstituted ester moieties derived from fatty acid materials having from about 18 to about 36 carbon atoms. The triglyceride gellant preferably has a preferred melting point of less than about 110° C., preferably between about 50° C. and 110° C. Preferred concentrations of the triglyceride gellants range from about 4% to about 20%, more preferably from about 4% to about 10%, by weight of the selected antiperspirant composition. Specific examples of preferred triglyceride gellants include, but are not limited to, tristearin, hydrogenated vegetable oil, trihydroxysterin (Thixcin® R, available from Rheox, Inc.), rape seed oil, castor wax, fish oils, tripalmiten, Syncrowax® HRC and Syncrowax® HGL-C (Syncrowax® available from Croda, Inc.). Other suitable glycerides include, but are not limited to, glyceryl stearate and glyceryl distearate.

Suitable amide gellants for use in the antiperspirant and deodorant compositions described herein include monoamide gellants, diamide gellants, triamide gellants, and combinations thereof, nonlimiting examples of which include cocoamide MEA (monoethanolamide), stearamide, oleamide, oleamide MEA, tallow amid monoethanolamide, and the n-acyl amino acid amide derivatives described in U.S. Pat. No. 5,429,816, issued to Hofrichter et al. on Jul. 4, 1995, which description is incorporated herein by reference. Other suitable amide gelling agents are described in U.S. Pat. No. 5,429,816, and U.S. patent application Ser. No. 08/771,183, filed Dec. 20, 1996, which descriptions are incorporated herein by reference. Concentrations of the amide gellants preferably range from about 0.1% to about 25%, more preferably from about 1% to about 15%, even more preferably from about 1% to about 10%, by weight of the selected antiperspirant or deodorant composition.

Other suitable gelling agents for use in the antiperspirant and deodorant compositions described herein include waxes or wax-like materials having a melt point of above 65° C., more typically from about 65° C. to about 130° C., examples of which include, but are not limited to, waxes such as beeswax, camauba, baysberry, candelilla, montan, ozokerite, ceresin, hydrogenated castor oil (castor wax), synthetic waxes, microcrystalline waxes. Castor wax is preferred within this group. Other high melting point waxes are described in U.S. Pat. No. 4,049,792, Elsnau, issued Sep. 20, 1977, which description is incorporated herein by reference.

Other suitable suspending or thickening agents for use in the antiperspirant compositions described herein include particulate suspending or thickening agents such as clays and colloidal pyrogenic silica pigments. Other known or otherwise effective particulate suspending or thickening agents can likewise be used in the substance compositions described herein. Concentrations of these suitable particulate thickening agents preferably range from about 0.001% to about 15%, more preferably from about 1% to about 15%, even more preferably from about 1% to about 8%, by weight of the selected antiperspirant composition. Colloidal pyrogenic silica pigments are preferred, a common example of which includes Cab-O-Sil®, a submicroscopic particulated pyrogenic silica.

Suitable clay suspending or thickening agents include montmorillonite clays, examples of which include bentonites, hectorites, and colloidal magnesium aluminum silicates. These and other suitable clay suspending agents are preferably hydrophobically treated, and when so treated will generally be used in combination with a clay activator. Non-limiting examples of suitable clay activators include propylene carbonate, ethanol, and combinations thereof. The amount of clay activator will typically range from about 25% to about 75% by weight of the clay, more typically from about 40% to about 60% by weight of the clay.

Liquid Carrier

The antiperspirant and deodorant compositions for use in the applicator of the present invention comprise a liquid carrier that is a liquid under ambient conditions, wherein the liquid carrier comprises one or more carrier liquid combinations or combinations of carrier liquids and dissolved carrier solids provided that any such combination is in liquid form under ambient conditions.

Concentrations of the liquid carrier in the antiperspirant and deodorant compositions will vary with the type of liquid carrier selected, the type of suspending or thickening agent used in combination with the liquid carrier, the type of product form desired, and so forth. Preferred concentrations of the liquid carrier ranges from about 1% to about 90%, preferably from about 10% to about 80%, more preferably from about 20% to about 70%, by weight of the selected antiperspirant or deodorant composition.

The antiperspirant and deodorant compositions described herein may be formulated as aqueous or anhydrous compositions. For an aqueous formulation, the compositions may further comprise from about 10% to about 75% by weight of water, preferably from about 10% to about 60% by weight of water, even more preferably from about 15% to about 50%, by weight of water. For an anhydrous formulation, the compositions contain less than about 10%, more preferably less than about 5%, even more preferably less than about 3%, even more preferably less than about 1%, most preferably zero percent, by weight of free or added water.

The liquid carrier comprises one or more liquid carriers suitable for topical application to human skin. These liquid carriers include any topically safe and effective organic, silicone containing or fluorine-containing, volatile or non-volatile, polar or non-polar carrier liquid, provided that the resulting combination of carrier materials form a solution or other homogenous liquid or liquid dispersion at the selected processing temperature of the composition. Processing temperatures for the antiperspirant and deodorant compositions typically range from about 28° C. to about 250° C., more typically from about 28° C. to about 110° C., and even more typically from about 28° C. to about 100° C.

The term "volatile" as used herein refers to those materials which have a vapor pressure as measured at 25° C. of from about 0.01 mmHg to about 6 mmHg, preferably from about 0.02 mmHg to about 1.5 mmHg, and an average boiling point at one atmosphere of pressure (1 atm) of less than about 250° C., preferably less than about 235° C., at 1 atmosphere (atm) of pressure. Conversely, the term "nonvolatile" as used herein refers to those materials which do not have a measurable vapor pressure under 1 atmosphere of pressure, at about 50% relative humidity, at about 25° C.

The term "nonpolar" as used herein refers to those materials which have a solubility parameter of less than 8.0 $(cal/cm^3)^{0.5}$, preferably from about 5.0 $(cal/cm^3)^{0.5}$ to less than 8.0 $(cal/cm^3)^{0.5}$, more preferably from 6.0 $(cal/cm^3)^{0.5}$ to about 7.60 $(cal/cm^3)^{0.5}$.

Solubility parameters for the liquid carriers and other materials described herein are determined by methods well known in the chemical arts for establishing the relative polar character of a solvent or other material. A description of solubility parameters and means for determining them are described by C. D. Vaughan, "Solubility Effects in Product, Package, Penetration and Preservation" 103 Cosmetics and Toiletries 47–69, October 1988; and C. D. Vaughan, "Using Solubility Parameters in Cosmetics Formulation", 36 J. Soc. Cosmetic Chemists 319–333, September/October, 1988, which descriptions are incorporated herein by reference.

Nonlimiting examples of suitable silicone-containing liquid carriers include volatile or nonvolatile silicones, modified or organofunctional silicones, and combinations thereof. The volatile silicone carriers may be cyclic, linear or branched chained silicones having the requisite volatility defined herein. The nonvolatile silicones are preferably linear silicones. The modified or organofunctional silicone carriers include polyalkylsiloxanes, polyalkyarylsiloxanes, polyestersiloxanes, polyethersiloxane copolymers, polyfluorosiloxanes, polyaminosiloxanes, and combinations thereof.

The modified silicone carriers are typically liquid under ambient conditions, and have a preferred viscosity of less than about 100,000 centistokes, more preferably less than about 500 centistokes, even more preferably from about 1 centistoke to about 50 centistokes, and most preferably from about 1 centistoke to about 20 centistokes. These modified silicone carriers are generally known in the chemical arts, some examples of which are described in 1 *Cosmetics, Science and Technology* 27–104 (M. Balsam and E. Sagarin ed. 1972); U.S. Pat. No. 4,202,879, issued to Shelton on May 13, 1980; U.S. Pat. No. 5,069,897, issued to Orr on Dec. 3, 1991; which descriptions are incorporated herein by reference.

Suitable modified silicone carriers include, but are not limited to, compounds or materials such as those defined hereinabove and which are generally characterized as follows: silicone polyethers or silicone glycols (such as dimethicone copolyol); silicone alkyl-linked polyethers (such as Goldschmidt EM-90 or EM-97); siloxane surfactants of a pendant/rake/comb configuration, silicone surfactants of a trisiloxane configuration, and silicone surfactants of an ABA/alpha-omega block copolymers (such as polyoxyalkylenes, polyoxyethylene or ethoxylated, polyoxyethylene/polyoxypropylene or ethoxylated/propoxylated); aromatic substituted silicone emollients (such as phenyl, alpha-methyl styryl, styryl, methylphenyl, alkylphenyl); silicone copolymers with other functional groups include: hydrogen, alkyl, methyl, amino, trifluoropropyl, vinyl, alkoxy, arylalkyl, aryl, phenyl, styryl, polyethers, esters, carboxylics; alkylmethyl siloxanes or silicone waxes (such as hexyl, octyl, lauryl, cetyl, stearyl); nonionic functional siloxane copolymers with terminal groups being silanol or trimethylsiloxy; nonionic functional siloxanes with backbone groups being trisiloxane or methicone linked; nonionic silicone surfactants; tetraethoxysilane; tetramethoxysilane; hexamethoxysilicone; oxmethoxytrisiloxane; silicone emulsifiers; silicone or siloxane resins, alkyl silicone resins, polyoxyalkylene silicone resins; MQ Resins such as Shiseido/Shin-etsu ,e.g. Japanese Patent Publication JP86143760 or from Walker Chem. 6MBH (described in EP722970); alkoxysiloxanes; alkoxysilanes; methicones (polymethylalkylsiloxanes); and combinations thereof.

Nonlimiting examples of suitable modified silicone carriers for use in the antiperspirant and deodorant compositions described herein include the following modified silicones available from Dow Corning: DC-556 Cosmetic Grade Fluid (phenyl trimethicone); DC-1784 Emulsion; DC-AF Emulsion; DC-1520-US Emulsion; DC-593 Fluid (Dimethicone [and] Trimethylsiloxysilicate); DC-3225C Fluid (Cyclomethicone [and] Dimethicone Copolyol); DC-1401 (Cyclomethicone [and] Dimethiconol); DC-5640 Powder; DC-Q2-5220 (Dimethicone Copolyol); DC Q2-5324 (Dimethicone Copolyol); DC-2501 Cosmetic Wax (Dimethicone Copolyol); DC-2502 Fluid (Cetyl Dimethicone); DC-2503 Wax (Stearyl Dimethicone); DC-1731 Volatile Fluid (Caproyl Trimethicone); DC-1-3563 (Dimethiconal); DC-X2-1146A (Cylcomethicone [and] Dimethiconol); DC-7224 (Trimethylsilylamodimethicone); DC-X2-1318 Fluid (Cyclomethicone [and] Vinyldimethicone); DC-QF1-3593A fluid (Trimethylsiloxysilicate) and combinations thereof.

Other nonlimiting examples of suitable modified silicone carriers include the following modified silicones available from General Electric: GE CF-1142 (Methylphenyl Siloxane Fluid); GE SF-1328; GE SF-1188 (Dimethicone copolyol); GE SF-1188A, and combinations thereof.

Other nonlimiting examples of suitable modified silicone carriers include the following modified silicones available from Goldschmidt: Abil EM-90 (silicone emulsifier); Abil EM-97 (polyether siloxane); Tegomer H-Si 2111, H-Si 2311, A-Si 2120, A-Si 2320, C-Si 2141, C-Si 2341, E-Si 2130, E-Si 2330, V-Si 2150, V-Si 2550, H-Si 6420, H-Si 6440, H-Si 6460 (Alpha-Omega Dimethicone Copolymers) and combinations thereof.

Other nonlimiting examples of suitable modified silicone carriers include the following: Masil 756 from PPG Industries (Tetrabutoxypropyl Trisiloxane); Silicate Cluster from Olin (Tris[tributoxysiloxy]methylsilane); silicone copolymer F-754 (dimethicone copolymer from SWS Silicones); and combinations thereof.

Non-limiting examples of suitable volatile silicones for use in the antiperspirant and deodorant compositions herein are described in Todd et al., "Volatile Silicone Fluids for Cosmetics", Cosmetics and Toiletries, 91:27–32 (1976), which descriptions are incorporated herein by reference. Preferred among these volatile silicones are the cyclic silicones having from about 3 to about 7, more preferably from about 4 to about 5, silicone atoms. Most preferably are those which conform to the formula:

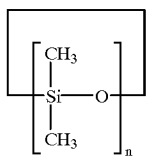

wherein n is from about 3 to about 7, preferably from about 4 to about 5, most preferably 5. These volatile cyclic silicones generally have a viscosity value of less than about 10 centistokes. All viscosity values described herein are measured or determined under ambient conditions, unless otherwise specified. Suitable volatile silicones for use herein include, but are not limited to, Cyclomethicone D-5 (commercially available from G. E. Silicones); Dow Corning 344, and Dow Corning 345 (commercially available from Dow Corning Corp.); GE 7207, GE 7158 and Silicone Fluids SF-1202 and SF-1173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V (available from Mazer); and combinations thereof.

The non-volatile silicone carriers for use in the antiperspirant and deodorant compositions described herein are preferably linear silicones which include, but are not limited to, those which conform to either of the formulas:

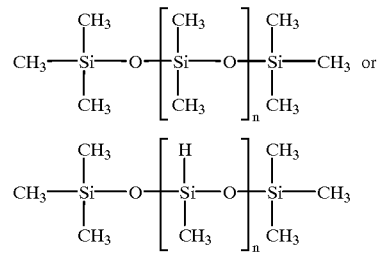

wherein n is greater than or equal to 1. These linear silicone materials will generally have viscosity values of up to about 100,000 centistoke, preferably less than about 500 centistoke, more preferably from about 1 centistoke to about 200 centistoke, even more preferably from about 1 centistoke to about 50 centistoke, as measured under ambient conditions. Examples of non-volatile, linear silicones suitable for use herein include, but are not limited to, hexamethyldisiloxane; Rhodorsil Oils 70047 (available from Rhone-Poulenc); Masil SF Fluid available from Mazer; Dow Corning 200, Dow Corning 225, Dow Corning 1732, Dow Corning 5732, Dow Corning 5750 (available from Dow Corning Corp.); SF-96, SF-1066 and SF18(350) Silicone Fluids (available from G.E. Silicones); Velvasil and Viscasil (available from General Electric Co.); Silicone L-45, Silicone L530, Silicone L-531 (available from Union Carbide); Siloxane F-221 and Silicone Fluid SWS-101 (available from SWS Silicones); and combinations thereof.

The antiperspirant and deodorant compositions preferably comprise a combination of volatile and nonvolatile silicone materials, more preferably a combination of volatile and nonvolatile silicone carrier liquids. Nonlimiting examples of suitable combinations of such silicone materials are described in U.S. Pat. No. 5,156,834 (Beckmeyer et al.), which description is incorporated herein by reference.

Nonlimiting examples of suitable polar organic liquid carriers for use in the antiperspirant and deodorant compositions described herein include mono and polyhydric alcohols, fatty acids, esters of mono and dibasic carboxylic acids with mono and polyhydric alcohols, polyoxyethylenes, polyoxypropylenes, polyalkoxylates ethers of alcohols, and combinations thereof. Preferably such liquid carriers are also water-immiscible liquids under ambient conditions. Other suitable water-immiscible, polar organic liquid carriers or solvents for use herein are described in Cosmetics, Science, and Technology, Vol. 1, 27–104, edited by Balsam and Sagarin (1972); U.S. Pat. No. 4,202,879 issued to Shelton on May 13, 1980; and U.S. Pat. No. 4,816,261 issued to Luebbe et al. on Mar. 28, 1989, which descriptions are incorporated herein by reference.

Other suitable liquid carriers for use in the antiperspirant and deodorant compositions described herein include anhydrous, water-miscible, polar organic liquid carriers or solvents, examples of which include short chain alcohols such as ethanol, and glycol solvents such as propylene glycol, hexylene glycol, dipropylene glycol, tripropylene glycol, and so forth. Other suitable similar solvents also include polyalkoxylated carriers such as polyethylene glycols, polyproylene glycols, combinations and derivatives thereof, and so forth. Non-limiting examples of polar solvents suitable for use herein are described in U.S. Pat. No. 5,429,816, which description is incorporated herein by reference. Other suitable polar solvents include phthalate co-solvents, benzoate co-solvents, cinnamate esters, secondary alcohols, benzyl acetate, phenyl alkane, and combinations thereof.

Nonlimiting examples of suitable nonpolar liquid carriers for use in the antiperspirant and deodorant compositions described herein include mineral oil, petrolatum, isohexadecane, isododecane, various hydrocarbon oils such as the Isopar or Norpar series available from Exxon Corp., the Permethyl series available from Persperse, and the Soltrol series available from Phillips Chemical, and any other polar or nonpolar, water-miscible, organic carrier liquid or solvent known or otherwise safe and effective for topical application to human skin.

Other suitable liquid carriers for use in the antiperspirant and deodorant compositions described herein include fluorine-containing liquid carriers such as fluorochemicals including fluorosurfactants, fluorotelemers, and perfluoropolyethers, some examples of which are described in Cosmetics & Toiletries, Using Fluorinated Compounds in Topical Preparations, Vol. 111, pages 47–62, (October 1996), which description is incorporated herein by reference. More specific examples of such liquid carriers include, but are not limited to, perfluoropolymethyl isopropyl ethers, perfluoropolypropylethers, acrylamide fluorinated telomer, fluorinated amide surfactants, perfluorinated thiol surfactants. Other more specific examples include, but are not limited to, the polyperfluoroisopropyl ethers available from Dupont Performance Chemicals under the trade name Fluortress® PFPE oils, and the series of fluorosurfactants available from Dupont Performance Chemicals under the trade name Zonyl® Fluorosurfactants.

The antiperspirant compositions described herein may further comprise dimethiconol as an optional liquid carrier. Preferred concentrations of the dimethiconol range from about 0.1% to about 50%, more preferably from about 1% to about 35%, even more preferably from about 2% to about 20%, by weight of the selected antiperspirant composition. Dimethiconols suitable for use as an optional liquid carrier include those corresponding to the formula:

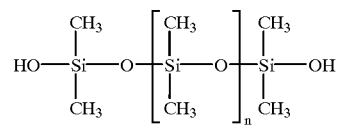

wherein n is number having a value of zero or greater, preferably from about 1 to about 100, more preferably from about 1 to about 50, even more preferably from about 1 to about 10. Nonlimiting examples of suitable dimethiconols include Masil® SFR 70, Mazol® SFR 18,000, Mazol® SFR 50,000, Mazol® SFR 100, Mazol® SFR 150,000, Mazol® SFR 750, Mazol® SFR 2000, and Mazol® SFR 3500, all available from PPG/Specialty Chemicals; Unisil SF-R available from Universal Preservative; and combinations thereof. Other available dimethiconols include Abil® OSW 12, OSW 13, Abil® OSW 15, and Abil® CK, all available from Goldschmidt; Dow Corning® 1401 Fluid, Dow Corning® Q2-1403 Fluid, Dow Corning® X2-1286 Fluid, all available from Dow Corning; Tri-Sil HGC 5000 available from Tri-K Industries; and combinations thereof.

Optional Components

The antiperspirant and deodorant compositions for use in the applicator of the present invention may further comprise one or more optional components which may modify the physical or chemical characteristics of the compositions or serve as additional "active" components when deposited on the skin. The compositions may also further comprise optional inert ingredients. Many such optional materials are known for use in antiperspirants, deodorants or other personal care compositions, and may be used in the antiperspirant and deodorant compositions described herein, provided that such optional materials are compatible with the essential materials described herein, or do not otherwise unduly impair product performance.

Nonlimiting examples of optional ingredients suitable for use in the antiperspirant and deodorant compositions described herein include pH buffering agents; additional emollients; humectants; dyes and pigments; medicaments; emulsifiers; chelants; distributing agents; preservatives; residue masking agents; wash-off aids; and soothing agents such as aloe vera, allantoin, D-panthenol, avocado oil and other vegetable oils, and lichen extract.

Rheology

One embodiment of the antiperspirant compositions described herein are antiperspirant creams which have a select rheology profile. The rheology profile as defined herein is a combination of select product delta stress (dyne/cm$^2$) and static yield stress (dyne/cm$^2$) values for the antiperspirant cream compositions. Methods for measuring or determining each of these essential characteristics of the rheology profile are described in detail hereinafter. Rheology methodologies are carried out at 27° C., 15% relative humidity, unless otherwise specified.

1. Methodology: delta stress and static yield stress

To determine delta stress and static stress yield values for the antiperspirant cream compositions, the compositions are analyzed using a Rheometrics Dynamic Stress Rheometer (available from Rheometrics Inc., Piscatawany, N.J., U.S.A) with data collection and analysis performed using Rhios software 4.2.2 (also available from Rheometrics Inc., Piscatawany, N.J., U.S.A.). The rheometer is configured in a parallel plate design using a 25 mm upper plate (available as part number LS-PELT-IP25 from Rheometrics Inc., Piscatawany, N.J., U.S.A.). Temperature control is set at 37° C. Analysis of the antiperspirant cream is performed in the "Stress Sweep: steady sweep" default test mode. Rheometer settings are initial stress (1.0 dyne/cm$^2$), final stress (63,930 dyne/cm$^2$), stress increment (100 dyne/cm$^2$), and maximum time per data point (5 seconds).

The term "static yield stress" as used herein refers to the minimum amount of stress (dyne/cm$^2$) that must be applied to the antiperspirant cream composition to move the upper plate of the Rheometrics Dynamic Stress Rheometer a distance of about 4.2 micro radians, in accordance with the analysis methods described herein. In other words, static yield stress represents the point in a stress sweep analysis (described herein) of a product at which point the rheometer is first capable of measuring product viscosity.

The term "delta stress" as used herein is determined by subtracting the static yield stress from the dynamic yield stress of a composition. The dynamic yield stress is the point at which the measured viscosity begins to rapidly decline. This can be easily determined by finding the last stress value where the increment between stress values is 100 dynes/cm$^2$. In other words, the delta stress of the composition represents the incremental amount of stress that must be applied to the composition, beyond the static yield stress of the composition, to substantially liquefy the composition.

The antiperspirant cream composition is evaluated for rheology characteristics after the composition has been packaged in the applicator device of the present invention. A section of the composition is carefully removed from the applicator so that the product is subjected to minimal shear, and especially so that it is not permitted to curl or otherwise reconfigure to a shape other than that of the section as it was removed from the composition. The section is carefully placed flat on the lower plate of the rheometer taking care to minimize the application of shear stress on the section during the placement. The area of the placed section is at least about the size of the upper plate to assure proper contact between the two plates during testing. The upper plate is then lowered toward the bottom plate, and positioned about 2 mm above the lower plate, and therefore about 1 mm from the product section which is positioned flat on the lower plate. The upper plate is further lowered at a minimal rate toward the lower plate, and positioned about 1.000 (+0.002) mm above the lower plate, at which point the product is gently positioned between and contacting each of the lower and upper plates. Excess product extending away from and around the parallel positioned plates is gently removed using a spatula, and taking care to subject the product positioned between plates to minimal or no further shear from the spatula. The solvent guard pad on the rheometer is saturated with the type of liquid carrier corresponding to that in the test product. The solvent guard is lowered over the parallel plates to prevent solvent loss from the test product that is positioned between the plates during analysis. The product is now ready for rheology analysis and determination of dynamic stress, static yield stress, and delta stress.

Product samples are subjected to rheological test and evaluation in accordance with the above described methodology. Data from the above described analysis can be plotted as viscosity (pascal-sec.) on a log scale versus linear applied stress (dyne/cm$^2$). The initial point at which the instrument measures a viscosity is the static yield stress (i.e. the lowest stress at which the instrument shows a non-zero viscosity). The dynamic yield stress is the point at which the measured viscosity begins to rapidly decline. This can be easily determined by finding the last stress value where the increment between stress values is 100 dyne/cm$^2$. The delta stress is then determined by subtracting the static yield stress from the dynamic yield stress.

The antiperspirant cream compositions have a static yield stress value of at least about 4,000 dyne/cm$^2$, more preferably at least about 8,000 dyne/cm$^2$, even more preferably at least about 40,000 dyne/cm$^2$. The maximum static yield stress values for the compositions are preferably less than about 120,000 dyne/cm$^2$, more preferably less than about 63,000 dyne/cm$^2$.

The delta stress value of the antiperspirant cream compositions is from about 300 dyne/cm$^2$ to about 8,000 dyne/cm$^2$, preferably from about 1,000 dyne/cm$^2$ to about 6,000 dyne/cm$^2$, more preferably from about 1,000 dyne/cm$^2$ to about 5,000 dyne/cm$^2$. A delta stress below the minimum level can result in solvent syneresis during shear force delivery means, whereas a value above the recited maximum can result in nonuniform spreading of the product onto the skin, and reduced spreadability on the skin, especially on hairy areas of the skin. The delta stress values, therefore, recited herein provide for a smooth creamy product that shows minimal or no solvent syneresis, spreads uniformly over the skin, and spreads especially well over and through hairy areas of the skin.

Skin Care Compositions

Another suitable category of substances believed suitable for use with the applicators of the present invention is the class of compositions generally referred to as skin care compositions. Such compositions include those intended to treat or modify human skin in terms of structure, condition, or appearance. By way of example only, and not to be interpreted as limiting, an area of current interest in the skin care area relates to compositions designed to address issues associated with the onset of skin wrinkles. Representative compositions in this area include salicylic acid technologies, such as those disclosed in commonly-assigned, published PCT applications WO 92/09737 and WO 92/09739, both published Jun. 10, 1993, and WO 92/08741, published Apr. 29, 1993. Another area of current interest is skin care compositions containing niacinamide, such as those disclosed in published PCT applications WO 96/17672, published May 15, 1997, and WO 97/06680, published Oct. 30, 1997. All of these publications are hereby incorporated herein by reference. Other suitable compositions include those disclosed in commonly-assigned U.S. Pat. Nos. 5,720,961, 5,707,635, 5,703,026, 5,700,451, 5,683,706, 5,674,509, and 5,665,364, the disclosures of which are hereby incorporated herein by reference.

Hair Care Compositions

The applicator of the present invention can also be used for topical application of hair care products to the hair. Hair care products which may be applied include shampoos, rinse-off conditioners, leave-on conditioning products, colorants, hair styling sprays, gels, and mousses.

Shampoos, used for cleansing hair, generally comprise one or more surfactants, thickeners or suspending agents, perftumes, and otionally conditioning or styling agents. Typical shampoos are disclosed in U.S. Reissue Pat. No. 34,584, Grote et al., issued Apr. 12, 1994; U.S. Pat. No. 5,756,436, Royce et al., May 26, 1998; U.S. Pat. No. 5,648,323, Coffindaffer et al., issued Jul. 15, 1997; U.S. Pat. No. 5,612,301, Inman, issued Mar. 18, 1997; U.S. Pat. No. 5,573,709, Wells, issued Nov. 12, 1996; U.S. Pat. No. 5,151,210, Steuri et al., issued Sep. 29, 1992; U.S. Pat. No. 4,704,272, Oh, issued Nov. 3, 1987; U.S. Pat. No. 4,705,681, Maes et al., issued Nov. 10, 1987; U.S. Pat. No. 4,387,090, Bolich Jr. Et al., issued Jun. 7, 1983; U.S. Pat. No. 4,379, 753, Bolich Jr., issued Apr. 12, 1983; and U.S. Pat. No. 4,345,080, Bolich Jr. et al., issued Aug. 17, 1982.

Hair conditioning products are generally used to apply conditioning agents to the hair after shampooing to improve detangling and/or provide soft hair feel. Typical rinse-off conditioners are disclosed in U.S. Pat. No. 5,667,771, Carballada et al., issued Sep. 16, 1997; U.S. Pat. No. 5,482,703, Pings, issued Jan. 9, 1996; U.S. Pat. No. 5,106,609, Bolich Jr. et al., issued Apr. 21, 1992; U.S. Pat. No. 5,104,646, Bolich Jr. et al., issued Apr. 14, 1992; and U.S. Pat. No. 4,387,090, Bolich Jr. issued Jun. 7, 1983. Typical leave-on conditioning products are disclosed in U.S. Pat. No. 5,674, 478, Dodd et al, Oct. 7, 1997.

Hair styling products, such as aerosol and non-aerosol hair sprays, mousses, and gels are disclosed in U.S. Pat. No. 5,750,122, Evans et al., May 12, 1998; U.S. Pat. No. 5,730,966, Torgerson et al., Mar. 24, 1998; U.S. Pat. No. 5,674,478, Dodd et al, Oct. 7, 1997; U.S. Pat. No. 5,658,557, Bolich Jr. et al., issued Aug. 19, 1997; U.S. Pat. No. 5,166,276, Hayama et al., issued Nov. 24, 1992; and U.S. Pat. No. 5,753,216, Leitch et al., issued May 19, 1998.

Hair coloring products have been generally disclosed in U.S. Pat. No. 5,679,114, Haning et al., issued Oct. 21, 1997; U.S. Pat. No. 5,597,386, Igarashi et al., issued Jan. 8, 1997; U.S. Pat. No. 5,435,810, Prota et al, issued Jul. 25, 1995; U.S. Pat. No. 5,356,439, Schultz et al., issued Oct. 18, 1994; U.S. Pat. No. 4,183,366, Bartuska et al., issued Jan. 15, 1980; and U.S. Pat. No. 4,200,432, Kalopissis et al., issued Apr. 29, 1980.

Other Substances

While much of the foregoing discussion has focused upon particular substances such as antiperspirant compositions which have proven suitable for use with applicators according to the present invention, it should be understood that the principles of the present invention are believed to apply to other applicator/substance combinations wherein the applicator is designed to account for the particular characteristics of the substance and the nature of the application environment. For example, it is believed that other compositions such as sunscreens, cooking products such as fats, oils, and shortenings, waxes such as shoe polishes and the like, and other substances may be suitable for use with applicators as described herein.

In accordance with the present invention, the substance utilized in combination with the deformable material exhibits a selection of physical properties which enable it to be dispensed from its protected orientation within the three-dimensional structure and applied to the target surface. Such dispensation may be partial, or substantially or totally complete in nature.

To facilitate such dispensing, substance properties which are believed to be important include the relative affinity of the substance for the target surface versus that for the deformable material and the apparent viscosity or flowability of the substance after activation of the three-dimensional structure. It is presently believed that the substance should preferentially adhere to the target surface to a greater extent than to the deformable material and/or to a greater extent than for other portions of the substance itself. Said differently, the substance has a greater affinity for the target surface than for itself and/or for the deformable sheet material.

Substances may inherently possess viscosity and flow characteristics which permit their liberation from their protected location within the sheet material or may require viscosity modification to permit liberation and dispersal. Viscosity modification may be obtained by the selection of substances which undergo a change in viscosity in response to the mode of activation selected. For example, for a mechanical activation such as a compressive force it may be desirable, and preferably, to employ substances which are commonly referred to as "shear-thinning" (pseudoplastic) substances. Examples of such substances include polymer solutions, many gels and pastes such as dentrifice and body creams, paints, gelled wood stains, etc. Other materials behave as shear-thinning materials only after a certain threshold shear (yield stress) is reached or exceeded. Such materials are commonly referred to as Bingham plastic materials, and one common example of a substance exhibiting such behavior is the type of condiment known as ketchup.

Some of the factors believed to influence the adhesion or affinity of the substance for the target surface include: electrostatic or electrical charges; chemical bonds via hydrogen bonding, covalent bonding, ionic bonding, partial ionic bonds (partial dipolar attraction), van der Walls forces, osmotic forces, etc.; capillary pressure (suction); adsorption; absorption; vacuum/suction; etc. Other important factors include the wettability of the substance upon the target surface, as reflected by the contact angle of the substance on the target surface.

To facilitate spreading or dispersal of the substance upon the target surface, particularly to counteract the tendency of the substance to remain in a localized distribution pattern given the localized orientation upon the deformable substance, it is presently preferred to utilize substances which are tailored so as to be wettable on the target surface. Other factors which may aid in dispersion or distribution of the substance upon the target surface include the use of substances which exhibit a shear-thinning behavior, as well as mechanical spreading action provided by the user of the composite sheet material to impart a lateral mechanical motion after activation but prior to removal of the deformable material from the target surface. Such lateral mechanical action may also provide additional interaction with the substance such as for shear-thinning substances and may provide additional benefits such as lathering, foam generation, scrubbing/abrasive action, etc.

Successful dispersal occurs when a portion of the deposited or dispensed substance subsequently coats a portion of the target surface where the substance was not originally deposited. Upon removal of the sheet material from the target surface, at least some of the substance remains located on the target surface, preferably in a substantially-uniform fashion.

As discussed above, a wide variety of substances may be selected for use in accordance with the principles of the present invention. Representative substances for illustrative purposes include cleansing agents such as soaps and detergents, emollients such as lotions, medicinal agents such as ointments, anti-inflammatory creams, etc., health and beauty care products, including antiperspirants, deodorants, cosmetics, fragrances, and the like. Other more diverse applications for such a sheet material include applicators for automotive and household products such as lubricants, colorants, protectants such as oils and waxes, adhesives, preservatives, and the like, as well as food-oriented applications such as condiments (mustard, ketchup, etc.).

Multiple substances may also be employed which are not only protected from inadvertent contact but segregated from one another initially (on the same face of, or on opposing faces of, the sheet material) and be commingled during the activation process or during subsequent dispensing and/or dispersion operations. Multiple diverse substances (ie: substances having different properties) may be included in either the same reservoir 50 or separate reservoirs 50." Such an arrangement may be particularly usefuil for substances which beneficially interact with one another (e.g., co-dispensing epoxies, catalyzed reactions, etc.) to provide additional fuinctionality with each other and/or with the target surface. It may also be desirable to provide for progressive or sequential substance delivery by tailoring the geometry of the applicator or substance properties to provide for initial application followed by additional progressive dispensing with the passage of time, increased pressure, etc.

3. Methods of Manufacture.

The applicators of the present invention may be manufactured in any manner suitable for the intended geometry and intended materials and substances involved. By way of example, for the presently preferred foam materials articulated above, the configuration of FIG. 1 may be manufactured by forming the plurality of apertures and reservoirs via thermal embossing with a heated die to the desired depth, then either injecting the substance into the reservoirs or flooding the substance into/onto the applicator and doctoring off the excess substance. A label or seal is then applied over the delivery zone and secured by thermal or adhesive means. The applicator may then be die cut to the final shape, or alternatively the die cutting step may be accomplished at the same time as the formation of the reservoirs, or any other suitable arrangement of steps. The substance may be heated or otherwise made flowable for such a process if necessary.

For an embodiment with a single reservoir such as that of FIG. 4, the application surface may be similarly manufactured, the backsheet may be peripherally joined by thermal or other means, and the substance may be injected into the reservoir from a single source or multiple sources if desired.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of tile invention.

What is claimed is:

1. An applicator for applying and distributing a substance onto a target surface, said applicator comprising:

(a) a substantially planar sheet of compressible, conformable material having opposed first and second surfaces and an interior region between said first and second surfaces, said sheet of material having a thickness between said first and second surfaces which decreases when said sheet of material is subjected to an externally-applied force in a direction substantially normal to said first surface, said material adapted to glide across the target surface to thereby expel the substance onto the target surface;

(b) at least one discrete reservoir extending inwardly of said first surface into the interior of said sheet of material;

(c) a substance at least partially filling said reservoir; and (d) at least one discrete aperture formed in said first surface, said aperture being in fluid communication with said reservoir;

whereby compression of said sheet of material via an externally-applied force substantially normal to said first surface expresses said product from said aperture and translational motion of said first surface relative to a target surface applies and distributes said product onto said target surface; wherein said applicator is made from all conformable elements.

2. The applicator of claim 1, wherein said applicator includes a plurality of apertures forming a delivery zone adjacent to one end of said applicator.

3. The applicator of claim 1, wherein said substance fills said reservoir to a level at least equal to said first surface.

4. The applicator of claim 1, wherein said reservoir defines an interior volume which decreases when said thickness is reduced by an externally-applied force.

5. The applicator of claim 1, wherein said applicator includes a plurality of apertures.

6. The applicator of claim 1, wherein said applicator includes a plurality of reservoirs.

7. The applicator of claim 1, wherein said applicator includes a plurality of apertures and a corresponding plurality of reservoirs, each of said apertures being in fluid communication with one of said reservoirs.

8. The applicator of claim 1, wherein said reservoir extends inwardly of said first surface into the interior of said sheet of material but does not penetrate said second surface.

9. The applicator of claim 1, wherein said reservoir extends inwardly of said first surface into the interior of said sheet of material a distance which is less than said thickness.

10. The applicator of claim 1, wherein said sheet material is resilient in compression.

11. The applicator of claim 1, wherein said sheet material is resilient in bending.

12. The applicator of claim 1, wherein said sheet material comprises a closed-cell foam material.

13. The applicator of claim 1, wherein said applicator includes a removable cover sheet for enclosing said aperture prior to use.

14. The applicator of claim 1, wherein said applicator includes a plurality of reservoirs and a corresponding plurality of apertures, and wherein said reservoirs include multiple diverse substances.

15. A method of making an applicator for applying and distributing a substance onto a target surface, said method comprising the steps of:

(a) providing a substantially planar sheet of compressible, conformable material having opposed first and second surfaces and an interior region between said first and second surfaces, said sheet of material having a thickness between said first and second surfaces which decreases when said sheet of material is subjected to an externally-applied force in a direction substantially normal to said first surface, said material adapted to glide across the target surface to thereby expel the substance onto the target surface;

(b) forming at least one discrete reservoir extending inwardly of said first surface into the interior of said sheet of material;

(c) at least partially filling said reservoir with a substance; and (d) forming at least one discrete aperture in said first surface, said aperture being in fluid communication with said reservoir;

wherein said applicator is made from all conformable elements.

16. The method of claim 15, wherein said reservoir is formed by thermal embossing.

17. The method of claim 15, wherein said substance is injected into said reservoir.

18. The applicator of claim 1, wherein said reservoir is a slot type reservoir.

19. The applicator of claim 1, wherein said reservoir is an aperture-channel type reservoir.

20. The applicator of claim 1, wherein said reservoir is an aperture-channel type reservoir positioned diagonally at a 45° angle.

21. The applicator of claim 1, wherein said reservoir has an aspect ratio of about 5 or below.

22. An applicator for applying and distributing a substance onto a target surface, said applicator comprising:

(a) a substantially planar sheet of compressible, conformable material having opposed first and second surfaces and an interior region between said first and second surfaces, said sheet of material having a thickness between said first and second surfaces which decreases when said sheet of material is subjected to an externally-applied force in a direction substantially normal to said first surface, said material adapted to glide across the target surface to thereby expel the substance onto the target surface;

(b) at least one discrete reservoir;

(c) a substance at least partially filling said reservoir; and (d) at least one discrete aperture which fully penetrates said first and second surfaces, said aperture being in fluid communication with said reservoir;

(e) a backing sheet peripherally joined to said second surface, wherein said reservoir is formed between said second surface and said backing sheet;

whereby compression of said sheet of material via an externally-applied force substantially normal to said first surface expresses said product from said aperture and translational motion of said first surface relative to a target surface applies and distributes said product onto said target surface;

wherein said applicator is made from all conformable elements.

23. An applicator for applying and distributing a substance onto a target surface, said applicator comprising:

(a) a substantially planar sheet of compressible, conformable material having opposed first and second surfaces and an interior region between said first and second surfaces, said sheet of material having a thickness between said first and second surfaces which decreases when said sheet of material is subjected to an externally-applied force in a direction substantially normal to said first surface, said market adapted to glide across the target surface to thereby expel the substance onto the target surface;

(b) at least one discrete reservoir;

(c) a substance at least partially filling said reservoir; and (d) at least one discrete aperture which fully penetrates said first and second surfaces, said aperture being in fluid communication with said reservoir;

(e) a backing sheet peripherally joined to said second surface, wherein said reservoir is formed between said second surface and said backing sheet;

whereby compression of said sheet of material via an externally-applied force substantially normal to said first surface expresses said product from said aperture and translational motion of said first surface relative to a target surface applies and distributes said product onto said target surface;

wherein said applicator does not contain a rigid member.

24. The applicator of claim 1, wherein said substance comprises:

(a) from about 0.1 to about 35 wt % a thickening agent selected from the group consisting of fatty alcohols, esters of fatty alcohols, fatty acids, hydroxy fatty acids, esters and amides of fatty acids or hydroxy fatty acids, ethers of fatty acids, ethoxylated fatty alcohols, ethoxylated fatty acids, waxes, cholesteric materials, dibenzylidene alditols, lanolinolic materials, other amide and polyamide gellants, and corresponding salts thereof, and mixtures thereof; and (b) from about 1% to about 90 wt % of a liquid carrier selected from the group consisting of silicones, modified silicones, mineral oil, petrolatum, hydrocarbon oils, and mixtures thereof.

* * * * *